United States Patent [19]

Batcho et al.

[11] Patent Number: 4,929,609

[45] Date of Patent: May 29, 1990

[54] 25,28-DIHYDROXYERGOCALCIFEROL AND 1,25,28-TRIHYDROXYERGOCALCIFEROL COMPOSITIONS THEREOF AND THEIR USE IN THE TREATMENT OF HYPERPROLIFERATIVE DISEASE

[75] Inventors: Andrew D. Batcho, North Caldwell, N.J.; Ronald L. Horst, Huxley, Iowa; Milan R. Uskokovic, Upper Montclair, N.J.; Joseph L. Napoli, Buffalo, N.Y.

[73] Assignees: Hoffmann-La Roche Inc., Nutley, N.J.; The United States of America as represented by the Department of Agriculture, Washington, D.C.

[21] Appl. No.: 272,170

[22] Filed: Nov. 14, 1988

Related U.S. Application Data

[63] Continuation of Ser. No. 24,944, Mar. 12, 1987, abandoned.

[51] Int. Cl.$^5$ ............................ A61K 31/59; C07J 9/00
[52] U.S. Cl. ..................................... 514/167; 552/653
[58] Field of Search ...................... 514/167; 260/397.2

[56] References Cited

U.S. PATENT DOCUMENTS 4,012,509 3/1977 Frank .................................. 514/167
4,069,321 1/1978 Jones et al. ......................... 514/167

OTHER PUBLICATIONS

Methods In Enzymology, vol. 123 (1986) p. 127–140; Napoli et al.

Primary Examiner—Joseph A. Lipovsky
Attorney, Agent, or Firm—George M. Gould; Bernard S. Leon; William G. Isgro

[57] ABSTRACT

Compounds of the formula

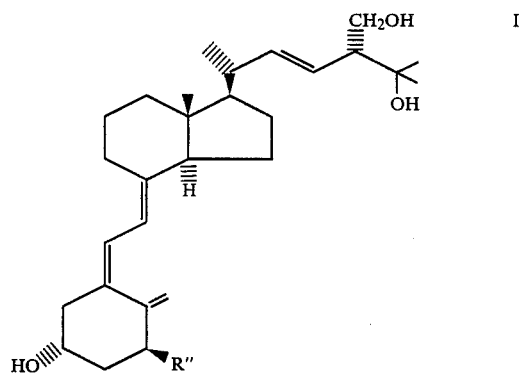

wherein R" is hydrogen or hydroxy, epimers at the 24-position of compounds of formula I, diastereomeric mixtures of compounds of formula I which are epimeric at the 24-position, and mixtures thereof, which are useful as agents for the treatment of psoriasis, and osteoporosis, are described.

17 Claims, No Drawings

25,28-DIHYDROXYERGOCALCIFEROL AND 1,25,28-TRIHYDROXYERGOCALCIFEROL COMPOSITIONS THEREOF AND THEIR USE IN THE TREATMENT OF HYPERPROLIFERATIVE DISEASE

This is a continuation of application Ser. No. 024,944 filed Nov. 12, 1987 now abandoned.

BRIEF SUMMARY OF THE INVENTION

The invention is directed to compounds of the formula

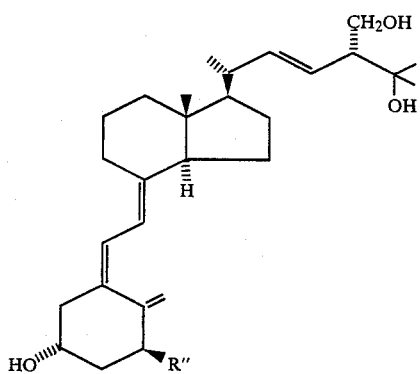

wherein R" is hydrogen or hydroxy, epimers at the 24-position of compounds of formula I, and diastereomeric mixtures of compounds of formula I which are epimeric at the 24-position.

Compounds of formula I and epimers thereof as described above are useful as agents for the treatment of skin diseases characterized by disorders of keratinization such as psoriasis. Compounds of formula I and epimers thereof as described above are also useful as agents for the treatment of disease states characterized by calcium imbalance such as osteoporosis.

DETAILED DESCRIPTION OF THE INVENTION

The invention relates to compounds of the formula

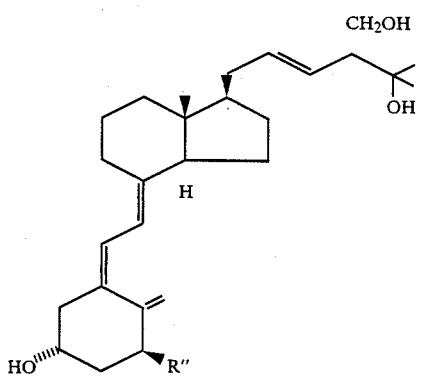

wherein R" is hydrogen or hydroxy, epimers at the 24-position of compounds of formula I, and diastereomeric mixtures of compounds of formula I which are epimeric at the 24-position.

Compounds of formula I and epimers thereof as described above are useful as agents for the treatment of hyperproliferative diseases of the skin. More specifically, compounds of formula I and epimers thereof as described above are useful as agents for the treatment of skin diseases characterized by disorders of keratinization such as Darier's disease or psoriasis. Compounds of formula I and epimers thereof as described above are also useful as agents for the treatment of disease states characterized by calcium imbalance such as osteoporosis.

The invention also comprises a composition comprising a compound of formula I or a mixture of the two compounds of formula I. Compositions of the invention also comprise a mixture of any of the following: compounds of formula I, epimers at the 24-position of compounds of formula I, and diastereomeric mixtures of compounds of formula I which are epimeric at the 24-position.

The invention also comprises a method for treating the above-mentioned disease states by administration of a compound of formula I, or a mixture of the two compounds of formula I. Methods of the invention also comprise administering a mixture of any of the following: compounds of formula I, epimers at the 24-position of compounds of formula I, and diastereomeric mixtures of compounds of formula I which are epimeric at the 24-position.

The invention also comprises a process for preparing compounds of formula I, and epimers thereof as described above.

In the formulas presented herein, the various substituents are illustrated as joined to the nucleus by one of the following notations: a solid line (◄) indicating a substituent which is above the plane of the molecule, and a dotted line (IIII) indicating a substituent which is below the plane of the molecule.

As used herein, (3β,5Z,7E,22E)-9,10-Secoergosta-5,7,10,(19) 22-tetraene-3,25,28-triol denotes the compounds of formula I wherein R" is hydrogen, that is, 25,28-dihydroxyergocalciferol. 1α,3β,5Z,7E,22E-9,10-secoergosta-5,7,10(19),22-tetraene-1,3,25,28-tetrol denotes the compound of formula I wherein R" is hydroxy, that is, 1,25,28-trihydroxyergocalciferol.

The compounds of formula I, epimers at the 24-position of compounds of formula I, and diastereomeric mixtures of compounds of formula I which are epimeric at the 24-position, are prepared as hereafter described, with particular reference to the Formula Scheme.

FORMULA SCHEME

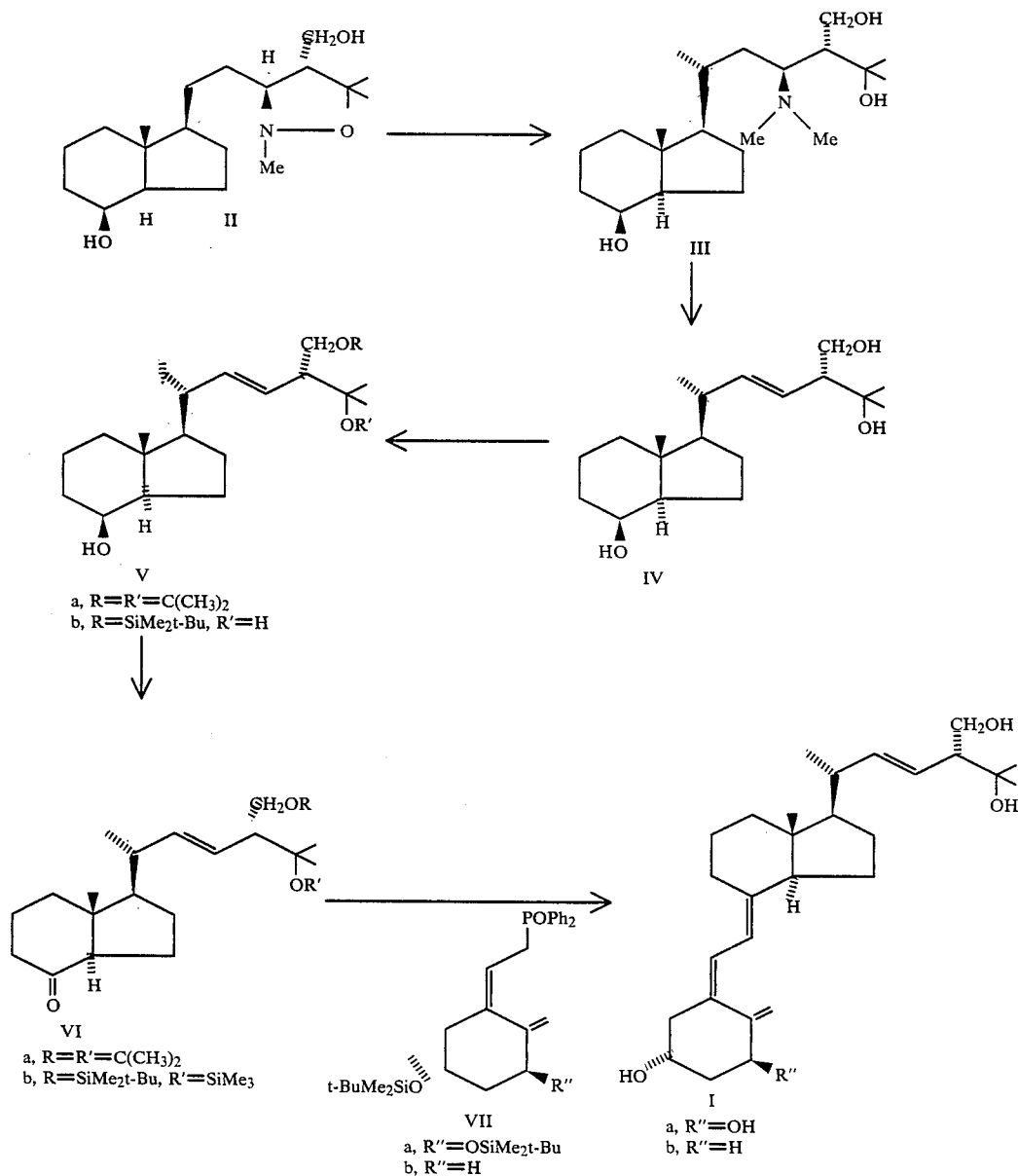

In the above Formula Scheme, the compound of formula II is converted to a compound of formula III by methylation of the nitrogen at room temperature in an inert solvent such as tetrahydrofuran with methyl iodide The resulting quaternary methiodide is treated with a reducing agent such as zinc dust in an acidic solvent such as aqueous acetic acid to achieve a compound of formula III.

The compound of formula III is methylated at the nitrogen with methyl iodide and treated with base to eliminate trimethylamine by a Hofmann elimination, thus yielding the compound of formula IV.

The compound of formula IV is treated with a protecting group such as 2,2-dimethoxypropane to form the acetonide, Va. Alternatively, the compound of formula IV is treated with t-butyldimethylsilyl chloride to form the silyl ether, Vb.

The compound of formula Va or Vb is treated with an oxidizing agent such as 2,2'-bipyridinium chloride to yield respectively a compound of formula VIa or VIb.

The compound of formula VIa is reacted with the compound of formula VIIa in an ether solvent such as anhydrous tetrahydrofuran at about −78° C. under an inert atmosphere such as argon and deprotected with cationic exchange resin to yield a compound of formula Ia. The compound of formula VIIa is a known compound or can be prepared according to known methods.

Analogously, a compound of formula VIb is reacted with a compound of formula VIIb to yield a compound of formula Ib. The compound of formula VIIb is a known compound or can be prepared according to known methods.

The compound of formula II is known as set forth in U.S. Pat. No. 4,508,651.

A compound of formula I, epimeric at the 24-position can be prepared by analogy to the above described procedure by starting with a compound of formula

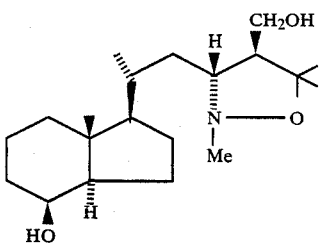

which is a known compound as hereinafter set forth.

A mixture of compounds of formula I diastereomeric at the 24-position can be prepared by analogy to the above described procedure by starting with a diastereomeric mixture of compounds II and II' which in turn can be prepared by known methods from the methyl esters,

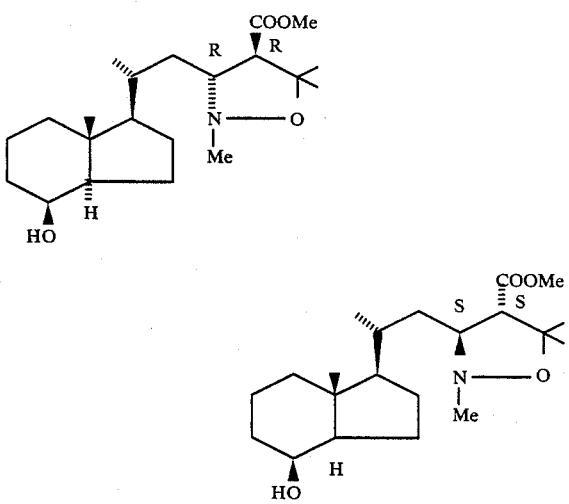

which methyl esters are disclosed in Baggiolini et al, J.O.C. 51, p. 3098–3108, (1986).

The examples hereinafter provided further illustrate the above formula scheme.

The compounds of formula I can be administered orally to warmblooded animals in dosages that are in the range of about 0.2 to 0.75 μg per day for the treatment of disease states characterized by calcium imbalance such as osteoporosis. The compounds of formula I can also be administered orally or topically to warmblooded animals for the treatment of hyperproliferative skin diseases and especially skin diseases characterized by disorders of keratinization such as Darier's disease or psoriasis. The compounds of formula I can be administered orally or topically for the treatment of dermatitis. Oral dosages in the treatment of the above skin diseases range from about 0.2 to 0.75 μg per day. Topical dosages for the treatment of skin diseases range from about 0.1 to about 1.0 μg per gram of topical formulation per day, more preferably 0.2 to 0.5 μg per gram of topical formulation.

The useful activity of compounds of formula I as agents for the treatment of skin diseases characterized by disorders of keratinization can be demonstrated by the following test procedures which are known in the art, and which are also set forth in The Society for Investigative Dermatology (1986) p. 709–714, Holick et al.

Effect of compounds of Formula I on the Morphologic Differentiation of Cultured Human Keratinocytes.

Keratinocyte Culture - Keratinocytes were grown in culture using a modification of the method of Rheinwald and Green. 3T3 cells were plated at $0.5 \times 10^5$ cells/35 mm tissue culture dish and 2 days later were lethally irradiated with a cobalt 60 source (5000 rads). Keratinocytes were obtained from human neonatal foreskin after overnight trypsinization at 4° C. and treatment with 0.02% EDTA. Keratinocytes were plated in 2 ml of serum-free medium per dish on the lethally irradiated 3T3 cells. Each experiment was perfumed on primary or secondary keratinocyte cultures obtained from different skin samples. The serum-free medium consisted of Dulbecco's modified Eagle's medium (DMEM) with high (1.8 mm) or low (<0.1 mm) concentration of calcium (M.A. Bioproducts, Walkersville, Md.) containing 7 growth factors; epidermal growth factor (25 ng/ml); hydrocortisone (203 ng/ml); insulin (5μg/ml); transfering (5μg/ml); prostaglandin $E_1$ (50 ng/ml); cholera toxin (0.1 μg/ml; Sigma Chemical Co., St. Louis, Miss.); and selenous acid (2ng/ml; Collaborative Research, Lexington, Mass.). Unless otherwise noted, cultures were grown in DMEM with a high calcium concentration. At 1 week in culture, hydrocortisone and cholera toxin were removed from the medium, and the dishes were washed with 0.02% EDTA to remove any remaining 3T3 cells. For the various assays, fresh medium containing vehicle alone that is <0.1% absolute ethanol and compound A or B at the concentrations given in table I below was added to each dish with each feeding. Feedings were done three times a week. For the control, fresh medium containing vehicle alone, that is, <0.1% absolute ethanol was used.

Quantitation of Morphologic Chances During Keratinocyte Differentiation. Beginning at 1 week in culture, groups of triplicate plates of keratinocytes were incubated with compounds A or B at the concentrations given in Table I below. After 1 or 2 weeks of dosing, the medium was removed from each culture, centrifuged, and resuspended for the counting of the desquamated floater cells. A hemacytometer was used to count the different cell types under a phase-contrast microscope. The attached cells were then trypsinized for 30–40 minutes with 0.1% EDTA and 0.1% trypsin and then neutralized with medium. The keratinocytes were centrifuged and resuspended in a known volume of medium. Duplicate aliquots were taken for counting the basal (small, rounded) and squamous (larger, irregular-shaped, flattened) cells. The remaining cells were centrifuged and treated with 10 mM Tris-HCl (pH 7.4) with 1% β-mercaptoethanol and 1% sodium dodecyl sulfate (SDS) at room temperature for 10 minutes. Only cells with cornified envelopes were present after this treatment. These were counted by hemacytometer.

A compound which induces the differentiation of basal cells to squamous and envelope cells is useful as an agent in the treatment of skin diseases characterized by disorders of keratinization such as psoriasis.

The results of the above tests are shown in TABLE I just below.

TABLE I

| Compound Concentration (M) | | Total | Number (× 10⁴) Basal | of Cells Squamous | Envelope |
| --- | --- | --- | --- | --- | --- |
| Control | | 117 ± 12 | 98 ± 9 | 17 ± 2 | 15 ± 1 |
| A | $10^{-10}$ | 95 ± 6 | 76 ± 5 | 17 ± 1 | 20 ± 1 |
| " | $10^{-8}$ | 78 ± 10 | 57 ± 7 | 18 ± 2 | 25 ± 2 |
| " | $10^{-6}$ | 80 ± 10 | 51 ± 7 | 26 ± 2 | 29 ± 2 |
| B | $10^{-10}$ | 96 ± 7 | 75 ± 4 | 18 ± 2 | 19 ± 2 |
| " | $10^{-8}$ | 85 ± 9 | 57 ± 5 | 25 ± 3 | 24 ± 2 |
| " | $10^{-6}$ | 81 ± 10 | 47 ± 8 | 31 ± 2 | 29 ± 2 |

In the table above, A is 1,25,28-trihydroxyergocalciferol, and B is 25,28-dihydroxyergocalciferol As already noted, the above test procedures indicate whether compounds are useful in the treatment of skin diseases characterized by disorders of keratinization such as, psoriasis.

From Table I it can be seen that compared to the control Compounds A and B of formula I, cause more basal cells to differentiate to squamous cells and envelope cells. Furthermore, increasing the concentrations of said compounds causes increasing percentages of basal cells to differentiate to squamous and envelope cells.

Accordingly, these results demonstrate that compounds of Formula I, that is, compounds A and B induce the differentiation of keratinocytes, and accordingly, are useful in the treatment to disorders of keratinization such as, Darier's disease, and especially psoriasis.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, adsorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the inflammation for the exertion of local action. Accordingly, the topical compositions include those pharmaceutical forms in which the compound is applied externally by direct contact with the skin. The topical dosage forms comprise gels, creams, lotions, ointments, powders, aerosols and other conventional forms for applying medication to the skin obtained by admixing either of the compounds with known pharmaceutical topical carrier materials. In addition to application to the skin, the topical compositions of this invention can also be employed in the treatment of inflammations of mucous membranes, where such membranes are accessible to topical application of medication. For example, the topical composition can be applied to the mucous linings of the mouth or lower colon.

Temperatures given herein are in degrees Celsius unless otherwise indicated.

EXAMPLE 1

Preparation of [1R-[1α(1R*,3S*,4R*), 3aβ,4α,7aα]]-2-[3-(Octahydro-4-hydroxy-7a-methyl-1H-inden-1-yl-3-methyl-1-(dimethylamino)propyl]-1,1-dimethyl-1,3-propanediol A solution of 3.53g of [3S-[3β,4α,3-[(2R*),1R*(1β,3aα, 4β,7aβ)]]]-3-[2-Octahydro-4-hydroxy-7a-methyl-1H-inden-1-yl)propyl)]-2,5,5-trimethyl-4-isoxazolindinemethanol, which is a known compound, 4.0 mL of freshly-distilled iodomethane, and 50 mL of freshly distilled tetrahydrofuran was stirred at room temperature under an argon atmosphere overnight. Precipitation began within 5 minutes. The solvent and excess iodomethane were removed on a rotary evaporator under reduced pressure and the residue was dissolved in a solution of 75 mL of glacial acetic acid and 25 mL of water. To the stirred solution was added 3.62g of zinc dust. After 5 hours the reaction mixture was cooled to 0°, and 400 mL of 4N sodium hydroxide followed by 100 mL of concentrated ammonium hydroxide was added. After extraction with 3×500 mL of ether which was washed in a counter-current manner with 100 mL of 1:1 concentrated ammonium hydroxide-water, the combined ether phases were dried ($Na_2SO_4$) and evaporated to give 3.60g of product. Recrystallization from 75 mL of acetonitrile (cooled to 0°) gave 3.0g (81%) of [1R-[1α(1R*,3S*,4R*), 3aβ,4α,7aα]]-2-[3-(octahydro-4-hydroxy-7a-methyl-1H-inden-1-y 1-3-methyl-1-(dimethylamino)propyl]-1,1-dimethyl-1,3-propanediol as white crystals. mp 169°–170°. An analytical sample had m.p. 169.5°–170.0° ($CH_3CN$), $[\alpha]_D 25°$ +16.2° (c 1.06, $CHCl_3$)

Anal. Calcd for $C_{21}H_{41}NO_3$: C, 70.94; H, 11.62; N, 3.94 Found: C, 71.18; H, 11.41; N, 4.14

EXAMPLE 2

Preparation of
[1R-[1α(1R*,2E*,3R*),3aβ,4α,7a]]-2-[3-(Octahydro-4-hydroxy-7a-methyl-1H-inden-1-yl)-3-methyl-1-propenyl]-1,1-dimethyl-1,3-propanediol To a solution of 101 mg of [1R-[1α(1R*,3S*,4R*)-,3aβ,4α, 7aα]]-2-[3-(octahydro-4-hydroxy-7a-methyl-1H-inden-1-yl-3-methyl-1-(dimethylamino)propyl]-1,1- dimethyl-1,3-propanediol in 1.0 mL of freshly distilled dry tetrahydrofuran under an argon atmosphere was added 200 mg of freshly distilled iodomethane. The solution was heated in an oil bath at 60° for 5 hours then left at room temperature overnight. The volatile components were removed on a rotary evaporator under reduced pressure. The residue was dissolved in 1.4 mL of 2N potassium hydroxide in ethanol and heated (under an argon atmosphere ) at 65° for 22 hours. The solvent was removed under reduced pressure, and to the residue was added 10 mL of water. Extraction with 3×25 mL of dichloromethane gave 78 mg of crude product. Medium pressure liquid chromatography (silica gel) using 1:2 hexanes-ethyl acetate as eluent afforded 30 mg (34%) of [1R-[1α(1R*,2E*,3R*),3aβ,4α,7aα]]-2-[3-(Octahydro-4-hydroxy7a-methyl-1H-inden-1-yl)-3-methyl-1-propenyl]-1,1-dimethyl-l,1,3-propanediol. An analytical sample had m.p. 143°–144° (CH₃CN), $[\alpha]_D^{25°}$ +19.5° (c 0.936, CHCl₃).

Anal. Calcd for $C_{19}H_{34}O_3$: C, 73.50; H, 11.04 Found: C, 73.24; H, 10.91

EXAMPLE 3

Preparation of
[1R-[1α(R*),3E(5R*)],3aβ,4α,7aα]-Octahydro-7a-methyl-1-[1-methyl-3-(2,2,4,4-tetramethyl-1,3-dioxan-5-yl)-2-propenyl -1H-inden-4-ol To a stirred solution of 246 mg of [1R-[1α(1R*,2E*,3R*), 3aβ,4α,7aα]-2-[3-(Octahydro-4-hydroxy-7a-methyl-1H-inden-1yl)-3-methyl-1-propenyl]-1,1-dimethyl-1,3-propanediol in 5 mL of acetone under an argon atmosphere, was added 15 mg of p-toluenesulfonic acid dihydrate. After one hour, 83 mg of 2,2-dimethoxypropane was a added followed by a second addition of 83 mg of 2,2-dimethoxypropane, 5.5 hours later. After stirring overnight (total 22 hours), the reaction mixture was poured into 50 mL of 10% sodium bicarbonate and extracted with 3×25 mL of dichloromethane. The combined organic phases were dried (Na₂SO₄), filtered, and evaporated under reduced pressure to give 259 mg of crude product. Medium pressure liquid chromatography on a 9 cm×25 mm column afforded 155 mg (55% conversion, 95% yield) of [1R-[1α(R*),3E(5R*)],3aβ,4α, 7aα-octahydro-7a-methyl-1-[1-methyl-3-(2,3,4,4-tetramethyl-1,3-dioxan-5-yl)-2-propenyl]-1H-inden-4-ol followed by 103 mg (44%) of starting material. An analytical sample of the [1R-[1α(R*),3E(5R*)],3aβ,4α,7aα]-Octahydro-7a-methyl-1-[1-methyl-3-(2,2,4,4-tetramethyl-1,3-dioxan-5-yl)-2-propenyl]-1H-inden-4-ol had mp 95°–96° (hexanes), $[\alpha]_D^{25°}$ +36.8° (c 0.929, CHCl₃).

Anal. Calcd for $C_{22}H_{38}O_3$: C, 75.38; H, 10.93. Found: C, 75.41; H, 10.97

EXAMPLE 4

Preparation of
[1R-[1α-[1R*,2E(5R*)]]-3aβ,4α,7aα]Octahydro-7a-methyl-1-[1-methyl-3-(2,2,4,4-tetramethyl-1,3-dioxan-5-yl)-2-propenyl]-1H-inden-4-one A solution of 114 mg of [1R-[1α[1R*,2E(5R*)]]-,3aβ,4α, 7aα]-octahydro-7a-methyl-l-[1-methyl-3-(2,2,4,4-tetramethyl-1,3 -dioxan-5-yl)-2-propenyl]-1H-inden-4-ol in 9 mL of methylene chloride was treated with 190 mg of powdered anhydrous sodium acetate and 380 mg of 2,2'-bipyridinium chlorochromate and the mixture stirred at room temperature for 2.5 hours. After this time, an additional 190 mg of 2,2'-bipyridinium chlorochromate was added and the stirring continued for 20 minutes. After quenching with water, the reaction mixture was extracted with ethyl acetate-ether (1:1). The combined organic phases were washed with water, brine, dried and evaporated to dryness. The crude residue was filtered by fast chromatography on silica eluting with hexane-ethyl acetate (4:1) to give 105 ml of [1R-[1α-[1R*,2E(5R*)]]-3aβ,4α,7aα]-Octahydro-7a-methyl-l-[1-methyl-3-(2,2,4,4-tetramethyl-1,3-dioxan-5-yl)-2-propenyl]-1H-inden-4-one as a white solid.

EXAMPLE 5

Preparation of
(1α,3β,5Z,7E,22E)-9,10-Secoergosta-5,7,10 (19),22-tetraene-1,3,25,28-tetrol A solution of 284 mg of [3S-(1Z,3α,5β)]-[2-[3,5-bis[[(1,1-dimethylethyl)-dimethylsilyl]oxy]-2-methylenecyclohexylidene]ethyl]diphenyl phosphine oxide in 8 mL of dry tetrahydrofuran was cooled at −78° C. and treated dropwise under argon with 0.275 mL of 1.6M of n-butyllithium in hexane. The resulting deep red solution was stirred for 5 minutes then treated dropwise at −78° C. with a solution of 105 mg of [1R-[1α[1R*,2E (5R*)]]-3aβ,4α,7aα]-octahydro-7a-methyl-1-[1-methyl-3-(2,2,4,4-tetramethyl-1,3-dioxan-5-yl)-2-propenyl]-1H-inden-4-one in 2 mL of anhydrous tetrahydrofuran and the stirring was continued under argon at −78° C. for 1.5 hours. After addition of 3 mL of a 1:1 mixture of 2N sodium potassium tartrate and 2N potassium bicarbonate, the reaction mixture was allowed to come to room temperature and extracted with ethyl acetate. The combined organic extracts were washed with brine, dried and evaporated to dryness. The residue was purified by fast chromatography through silica (eluent: hexane-ethyl acetate, 10:1) to give 180 mg of product. This was dissolved in a mixture of 0.5 mL of methylene chloride and 10 mL of methanol, treated with 4.0 g of AG50W-X4 cation exchange resin (Bio-Rad Laboratories, Richmond, Calif. 94804) and the resulting suspension stirred under argon at room temperature for 17 hours. After filtration and washing of the resin with methanol, the combined filtrates were evaporated to dryness. The residue was purified by rapid chromatography through silica (eluting initially with hexane-ethyl acetate 1:5, then with ethyl acetate) to give 106 mg (79%) overall yield) of (1α,3β,5Z,7E,2-2E)-9,10-Secoergosta-5,7,10(19),22-tetraene- 1,3–25,28-tetrol as a white solid, mp 173°–174° C. (after recrystallization from methyl formate): $[\alpha]_D^{25°}$ +53.5(c 0.5, EtOH), ¹HNMR (200 MHz, CD₃OD) δ 0.60 (s, 3H), 1.07 (d, J=6.8 Hz, 3H), 1.16 (s, 3H), 1.18 (s, 3H), 3.59 (dd, J=7.6, 11.0 Hz, 1H), 3.85 (dd, J=7.6, 11.0 Hz, 1H), 4.15 (m, 1H)), 4.37 (m, 1H), 4.88 (br s, 1H), 5.22 (dd, J=8.0 15.6 Hz, 1H), 5.28 (br s, 1H), 5.42 (dd J=8.0, 15.6 Hz, 1H), 6.08 (d, J=11.8 Hz, 1H), 6.33 (d, J=11.8 Hz, 1H) ppm

EXAMPLE 6

Preparation of [1R-[1α(1R*, 2E*,3R*),3aβ,4α,7aα]][1.5-dimethyl-4[[[(1.1-dimethylethyl)dimethvl]silyloxy]methyl]-2-hexenyl]-5-hydroxy-3-octahydro-1H-indan-4-ol.

To a magnetically stirred solution 100 mg of [1R-[1α(1R*, 2E*,3R*),3aβ,4α,7aα]]-2-[3-(Octahydro-4-hydroxy-7a-methyl-1Hinden-1-yl)-3-methyl-1-propenyl]-1,1-dimethyl-1,3-propanediol in 2.0 mL of dry pyridine at room temperature under an argon atmosphere was added 73 mg of tert.-butyldimethylsilyl chloride. After 3 hours at room temperature 0.5 mL of water was added. Stirring was continued for 15 minutes then the reaction mixture was poured into 20 mL of 10% sulfuric acid at 0° and extracted with 3×20 mL of dichloromethane. The dichloromethane phases were back-washed with 20 mL of 10% sodium bicarbonate solution, dried (Na$_2$SO$_4$), filtered, and evaporated to give 138 mg of residue. Medium pressure liquid chromatography (silica gel) on eluting with 4:1 hexanes-ethyl acetate afforded 113 mg of [1R-[1α(1R*,2E*,3R*), 3aβ,4α, 7aα]]-[1,5-dimethyl-4-[[[(1,1-dimethylethyl)-dimethyl]-silyloxy]methyl]-2-hexenyl]-5-hydroxy-3-octahydro-1H-indan-4-ol.

EXAMPLE 7

Preparation of
[1R-[1α(1R*,2E,4R*),3aβ,4α,7aα]-Octahydro-1-[1,5-dimethyl-4-[[(1,1-dimethylethyl)-dimethyl-silyl]-oxy[-methyl]-5-[(trimethylsilyl)oxy]-7a-methyl-4H-inden-4-one A solution of 100 mg of [1R-[1α(1R*,2E,4R*)-,3aβ,4α, 7aα]-octahydro-1-[1,5-dimethyl-4-[[(1,1-dimethylethyl)dimethylsilyl]oxymethyl]-5-hydroxy-2-hexenyl]-7a-methyl-1H-inden-4-ol in 6 mL of dry methylene chloride was treated with 138 mg of anhydrous sodium acetate and 276 mg of 2,2'-bipyridinium chlorochromate and the mixture stirred at room temperature for 2 hours. After this time, an additional 140 mg of 2,2'-bipyridinium chlorochromate was added and the stirring was continued for an additional 2.5 hours. Water was then added to the reaction mixture which was extracted from a mixture of ether and ethyl acetate (1:1). The combined organic phases were washed with water, 1N hydrochloric acid (under ice cooling), then water, dried and evaporated to dryness. The crude residue was purified by rapid chromatography on silica, eluting with hexane-ethyl acetate (3:1) to give 95 mg of pure intermediate. This was dissolved in 6 mL of methylene chloride, treated with 0.135 mL of 1-(trimethylsilyl)imidazole and stirred under argon at room temperature for 18 hours. Water 2 mL was then added and after stirring for 20 minutes the resulting mixture extracted with ethyl acetate. The combined extracts were washed with water and brine, dried and evaporated to dryness. The residue was purified by fast filtration through silica, eluting with hexane-ethyl acetate (5:1) to give 106 mg (91% overall yield) of [1R-[1α(1R*,2E,4R*),3aβ,4α, 7aα]-Octahydro-1-[1,5-dimethyl-4-[[(1,1-dimethylethyl)-dimethyl silyl]oxymethyl]-5-[(trimethylsilyl)oxy]-7a-methyl-4H-inden-4-on as a colorless liquid.

EXAMPLE 8

Preparation of
(3β,5Z,7E,22E)-9,10-Secoergosta-5,7,10(19),22-tetraene-3,25,28-triol A solution of 145 mg of (5R,1Z)-[2-[[(1,1-dimethylethyl) dimethylsilyl]oxy]-2-methylenecyclohexylidene]-ethyl]diphenyl phosphine oxide in 7 mL of anhydrous tetrahydrofuran was cooled at −78° C. and treated dropwise under argon with 0.194 mL of 1.6M of n-butyllithium in hexane. The resulting deep red solution was stirred for 5 minutes and then treated dropwise at −78° C. with a solution of 106 mg of [1R-[1α(1R*,2E,4R*),3aβ,4α, 7aα]octahydro-1-[1,5-dimethyl-4-[[(1,1-dimethyl)dimethylsilyl] oxymethyl]-5-[(trimethylsilyl)oxy]-7a-methyl-4H-inden-4-one in 2 mL of anhydrous tetrahydrofuran over 10 minutes and the stirring was continued under argon at −78° C. for 1.5 hours. After the addition of 5 mL of a 1:1 mixture of 2N sodium potassium tartrate and 2N potassium bicarbonate the reaction mixture was allowed to come to room temperature and extracted with ethyl acetate. The combined organic extracts were washed with brine, dried and evaporated to dryness. The residue was purified by fast chromatography through silica gel elution 20:1 hexane-ethyl acetate). The so-obtained intermediate was dissolved in 7 mL of anhydrous tetrahydrofuran, treated with 1.4 mL of a 1M solution of tetrabutylammonium fluoride in tetrahydrofuran and stirred at room temperature under argon for 16 hours. After partial evaporation of the solvent in vacuo the residue was diluted with 15 mL of water and extracted with ethyl acetate. The combined organic extracts were washed with water then brine, dried and evaporated to dryness. The crude product was purified by fast chromatography through silica (eluent, hexane-ethyl acetate 1;3) to give 86 mg (65% overall yield) of pure (3β,5Z,7E,22E)-9,10-Secoergosta-5,7,10(19),22-tetraene-3,25,28-triol as a white solid, mp 144°–145° C. (after recrystallization from methyl formate); $[α]_D^{25°}$ +46.8 (c 0.2, EtOH), $^1$H NMR (400 MHz, CD$_3$OD) 0.58) (s.H) 1.06) (d J=7.0 Hz, 3H), 1.16 (s, 3H), 1.18 (s, 3H), 3.60 (dd. J=8.0 11.2 Hz, 1H), 3.76 (m, 1H), 3.85 (dd J=8.0, 11.2 Hz, 1H), 4.77 (br s, 1; H), 5.04 (br s, 1H), 5.24 (dd J=8.0, 15.2 Hz, 1H) 5.41 (dd, J=8.0, 15.2 Hz, 1H), 6.04 (d, J=12.0 Hz, 1H), 6.23 (d, J=12.0 Hz, 1H) ppm

EXAMPLE 9

0.00001% and 0.0001% Cream

The following is the quantitative composition of drug:

| Ingredients | g/kg | g/kg | Reasonable Variations |
|---|---|---|---|
| Compound A* | 0.0001 | 0.001 | — |
| Glyceryl Monostearate S.E. | 105.145 | 104.635 | 80–120 |
| Polysorbate 60 | 20.00 | 20.00 | 15–25 |
| Cetyl Alcohol | 50.00 | 50.00 | 40–60 |
| Petrolatum | 70.00 | 70.00 | 50–90 |
| Methyl Paraben | 1.50 | 1.50 | 1.25–1.75 |
| Propyl Paraben | 0.50 | 0.50 | 0.4–0.6 |
| Propylene Glycol | 200.00 | 200.00 | 150–250 |
| Purified Water | 568.05 | 568.05 | 475–575 |

*3% excess of drug.

1. Dissolve Compound A in propylene glycol add methyl and propyl paraben, and water and heat to 70° C.
2. Melt glyceryl monostearate S.E., cetyl alcohol and petrolatum and add polysorbate 60 and heat to 70° C.
3. Mix Part 1 and Part 2 with constant stirring and Cool to room temperature.

Compound A is as described above.

EXAMPLE 10

CAPSULE FORMULATION

| Ingredients | mg/capsule | |
|---|---|---|
| Compound B | 0.0001 | 0.00075 |
| Fractionated Coconut Oil | 198.9895 | 198.980 |
| Butylated Hydroxy | 0.01 | 0.01 |

| Ingredients | mg/capsule | |
|---|---|---|
| Anisol (BHA) | | |
| Ascorbyl Palmitate | 1.0 | 1.0 |

1. Dissolve Compound B is fractionated coconut oil, add BHA and Ascorbyl palmitate.
2. Fill in soft gelatin capsule.

Compound B is as described above.

We claim:

1. A compound of the formula

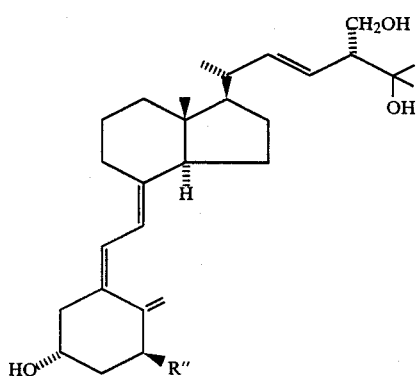

wherein R″ is hydrogen or hydroxy, an epimer at the 24-position of a compound of formula I, or a diastereomeric mixture of compounds of formula I which are epimeric at the 24-position.

2. A compound in accordance with claim 1 wherein R″ is hydrogen.
3. A compound in accordance with claim 1 wherein R″ is hydroxy.
4. A composition for the treatment of hyperproliferative diseases of the skin comprising an effective amount of a compound of the formula

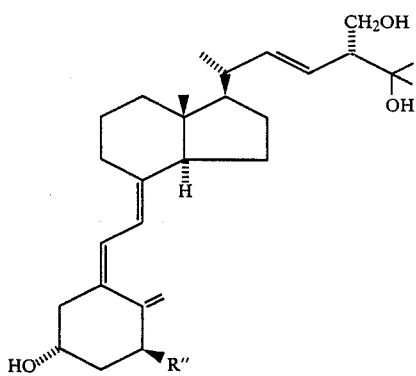

wherein R″ is hydrogen or hydroxy, an epimer at the 24-position of a compound of formula I, a diastereomeric mixture of compounds of formula I which are epimeric at the 24-position or a mixture thereof and a pharmaceutically acceptable carrier material.

5. A composition in accordance with claim 4 wherein R″ is hydrogen.
6. A composition in accordance with claim 4 wherein R″ is hydroxy.
7. A composition in accordance with claim 4 suitable for oral administration.
8. A composition in accordance with claim 7 wherein the amount of compound of formula I is from about 0.2 to about 0.75 μg.
9. A composition in accordance with claim 4 suitable for topical administration.
10. A method for the treatment of hyperproliferative diseases of the skin which comprises administering to a warm blooded animal in need of such treatment an effective amount of a compound of the formula

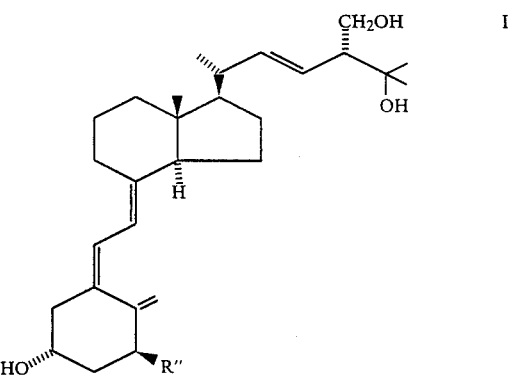

wherein R″ is hydrogen or hydroxy, an epimer at the 24-position of a compound of formula I, or a diastereomeric mixture of compounds of formula I which are epimeric at the 24-position, or a mixture thereof.

11. A method in accordance with claim 10, wherein the hyperproliferative disease of the skin is a disorder of keratinosis.
12. A method in accordance with claim 11, wherein the disorder of keratinosis is psoriasis.
13. A method in accordance with claim 12, wherein R″ is hydrogen.
14. A method in accordance with claim 12, wherein R″ is hydroxy.
15. A method in accordance with claim 12, wherein the composition is administered topically.
16. A method in accordance with claim 12, wherein the composition is administered orally.
17. A method in accordance with claim 16 wherein the amount of a compound of formula I administered is from about 0.2 to about 0.75 μg.

* * * * *